United States Patent
Li et al.

(10) Patent No.: US 9,359,314 B2
(45) Date of Patent: Jun. 7, 2016

(54) THIAZINE AMIDE DERIVATIVE AND PHARMACEUTICAL COMPOSITION AND USE THEREOF

(75) Inventors: Song Li, Beijing (CN); Junhai Xiao, Beijing (CN); Dan Han, Beijing (CN); Wu Zhong, Beijing (CN); Lili Wang, Beijing (CN); Zhibing Zheng, Beijing (CN); Yunde Xie, Beijing (CN); Xinbo Zhou, Beijing (CN); Xingzhou Li, Beijing (CN); Xiaokui Wang, Beijing (CN); Dan Jiang, Beijing (CN); Wei Chen, Beijing (CN); Hongying Liu, Beijing (CN)

(73) Assignee: Institute Of Pharmacology And Toxicology Academy Of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 14/423,205

(22) PCT Filed: Aug. 24, 2012

(86) PCT No.: PCT/CN2012/080539
§ 371 (c)(1),
(2), (4) Date: Feb. 24, 2015

(87) PCT Pub. No.: WO2014/029102
PCT Pub. Date: Feb. 27, 2014

(65) Prior Publication Data
US 2015/0203460 A1    Jul. 23, 2015

(51) Int. Cl.
*C07D 279/12* (2006.01)
(52) U.S. Cl.
CPC .................................. *C07D 279/12* (2013.01)
(58) Field of Classification Search
CPC ...................................................... C07D 279/12
USPC ...................................... 544/58.4; 514/227.5
See application file for complete search history.

(56) References Cited

U.S. PATENT DOCUMENTS 7,304,057 B2 * 12/2007 Li et al. ........................ 514/227.5
2005/0130958 A1    6/2005  Li et al.

FOREIGN PATENT DOCUMENTS

| CN | 1422852 A | 6/2003 |
|----|-----------|--------|
| CN | 102675244 A | 9/2012 |

OTHER PUBLICATIONS

Sun et al. Biophysical Journal (2003), 85(5), 3194-3201.*
Nie et al. Chinese Chemical Letters (2005), 16(2), 163-166.*
Li et al. Protein and Peptide Letters (2002), 9(5), 459-463.*
International Search Report (ISR) for PCT/CN2012/080539; I.A. fd: Aug. 24, 2012, mailed May 2, 2013, State Intellectual Property of of the P.R. China, Beijing, China.
International Preliminary Report on Patentability (IPRP) including the Written Opinion of the International Searching Authority (PCT Rule 44bis) for PCT/CN2012/080539; I.A. fd: Aug. 24, 2012, issued Feb. 24, 2015, by the International Bureau of WIPO, Geneva, Switzerland.
Nie, Ah et al., "Drug discovery based on the structure of FKBP 12: Design, synthesis and evaluation of L-1,4-thiazane-3-carboxylic acid derivatives as neuroimmunophilin ligands," Science in China, Series, B: Chemistry, Jun. 2007, 50(3):405-417, Chinese Academy of Sciences, Science Press, Beijing, China.
Nie, Ah et al., "Drug discovery based on the structure of FKBPs: Design, Synthesis and Evaluation of L-1,4-thiazane-3-carboxylic acid derivatives as neuroimmunophilin ligands," Chinese Chemical Letters, 2005, 16(2): 163-166, Chinese Chemical Society, Beijing, China.

* cited by examiner

*Primary Examiner* — Kahsay Habte
(74) *Attorney, Agent, or Firm* — Sterne, Kessler, Goldstein & Fox PLLC

(57) ABSTRACT

The present invention relates to a thiazine amide derivative and a pharmaceutical use thereof, and particularly to a compound of formula I (in the formula, variables are as described in the specification), a pharmaceutically acceptable salt, solvate or hydrate thereof. The present invention further relates to a method for preparing the compound, a pharmaceutical composition containing the compound, and a method or use thereof for prevention or treatment of neurodegenerative diseases.

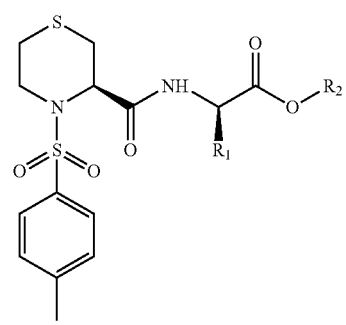

5 Claims, No Drawings

THIAZINE AMIDE DERIVATIVE AND PHARMACEUTICAL COMPOSITION AND USE THEREOF

FIELD OF THE INVENTION

The present invention relates to a thiazine amide derivative, a pharmaceutical composition containing the compound, and a method or use thereof for prevention or treatment of neurodegenerative disease.

BACKGROUND OF THE INVENTION

Neurodegenerative disease is the disease caused by progressive lesions of nervous system, including Alzheimer's disease, Parkinson's disease. Huntington's disease, amyotrophic lateral sclerosis (ALS), ischemic or hemorrhagic stroke, etc. Since the cause of the disease is complex and the pathogenic mechanism is not very clear, there is no effective therapeutic at present.

FKBPs, which is named because of its binding with immunosuppressant FK506, is an important mediator enabling FK506 to exert immunosuppressive function, however, its physiological function has not yet been fully explained. In 1992, Steiner J. P. et al. found that the concentration of FKBPs (FKBP family) in brain and periphery nervous system was much higher than that in immune tissues, which leads to speculation that there is a certain relationship between FKBPs and nervous system. The research results of Dawson, et al. showed that FK506 could block nervous excitotoxicity caused by activation of NMDA receptor by glutamate. It is speculated that FK506 might increase phosphorylation of nitric oxide synthase (NOS) after inhibiting Calcineurin, and inhibit the catalytic activity of NOS, thus prevent neurons from being injured by NO. In addition, researches showed that GAP43, which was closely related to neurons, was also a substrate of Calcineurin. The regeneration of injured facial nerve and sciatic nerve always accompanied with obvious increase in mRNA level of GAP43, meanwhile, the mRNA level of FKBPs is correspondingly increased. These research results indicated that FKBPs might have certain relationship with the growth of nerves, and finally inspired people to find out organic small-molecular compounds, which were capable of promoting the growth of nerves, from ligands of FKBPs, and FKBPs were therefore also called as neuro-immunophilins.

Directed by the view mentioned above, in 1994, the study of Lyons, et al. showed that the immunosuppressant FK506 had significant in-vitro activity of promoting the growth of the nerves, and initiated the research on organic small-molecular nerve growth promoter. Although the mechanism of promoting the growth and protection of nerves by the ligands of FKBPs family had not been completely understood, more and more researches showed that FKBPs participated in and mediated the process. The biological evaluations, including in-vitro tests (chicken embryonic dorsal root ganglion growth, PC12 cell differentiation, oxidative injuries of nerve cell strains, etc.) and a variety of animal models (a rat peripheral sciatic nerve injury model, a diabetic rat peripheral nerve degeneration model, a Parkinson's disease animal model, an Alzheimer's disease animal model and the like), showed that some compounds designed and synthesized based on the structure of FKBPs had significant effects of promoting the growth and protection of nerves. The typical compound is GPI11485 of Guilford Pharmaceuticals Inc., according to the company, the phase II clinical researches of GPI1485 as a therapeutic for prevention or treatment of Parkinson's disease and stroke has been completed, and the phase III clinical researches are also ongoing. Simultaneously, a large number of high-activity compounds continue to emerge, thereby enabling FKBPs to become important targets of the pharmaceuticals for prevention or treatment of the neurodegenerative disease.

Chinese patent application No. 01142744.2 (Substituted hexa azacyclo compounds and their use as neuroregulator) discloses FKBP ligands with brand-new structure and capable of promoting nerve regeneration, wherein the compound 4 is an optimal compound. However, researches showed that, the compound had poor blood-brain barrier permeability, and due to the low melting point and being oil state at normal temperature, the compound was not suitable for preparation of pharmaceuticals for prevention or treatment of neurodegenerative disease.

Thus, there is a need to find and develop a novel compound with enhanced permeability of blood-brain barrier and useful in prevention or treatment of neurodegenerative disease.

SUMMARY OF THE INVENTION

The present invention aims at providing a new thiazine amide derivative, a pharmaceutical composition containing the compound, and a method or use thereof for prevention or treatment of neurodegenerative disease.

The first aspect of the present invention provides a thiazine amide derivative having a structure of formula I,

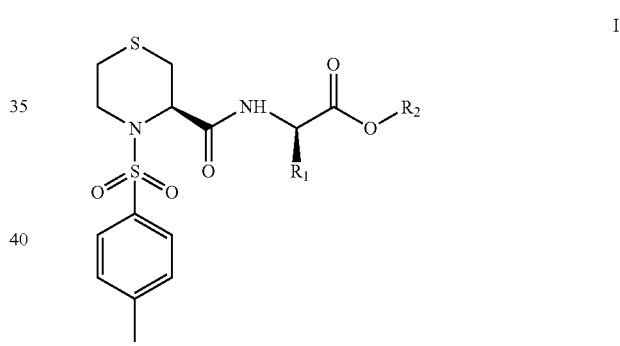

or a pharmaceutically acceptable salt, solvate or hydrate thereof, wherein, $R_1$ is hydrogen or straight or branched chain alkyl having 1-6 carbon atoms; and $R_2$ is straight or branched chain alkyl having 1-4 carbon atoms or phenyl-substituted straight or branched alkyl having 1-4 carbon atoms.

In an embodiment, the present invention provides a thiazine amide derivative having a structure of formula I or a pharmaceutically acceptable salt, solvate or hydrate thereof, wherein, $R_1$ is the hydrogen or straight or branched chain alkyl having 1-4 carbon atoms; and $R_2$ is straight or branched chain alkyl having 1-4 carbon atoms or phenyl-substituted straight or branched chain alkyl having 1-4 carbon atoms.

In another embodiment, the present invention provides a thiazine amide derivative having a structure of formula I or a pharmaceutically acceptable salt, solvate or hydrate thereof, wherein, $R_1$ is straight or branched chain alkyl having 1-4 carbon atoms; and R₂ is straight or branched chain alkyl having 1-4 carbon atoms or phenyl-substituted straight or branched chain alkyl having 1-4 carbon atoms.

In another embodiment, the present invention provides a thiazine amide derivative having a structure of formula I or a pharmaceutically acceptable salt, solvate or hydrate thereof, wherein, R₁ is straight or branched chain alkyl having 1-4 carbon atoms; and R₂ is straight or branched chain alkyl having 1-4 carbon atoms.

In another embodiment, the present invention provides a thiazine amide derivative having a structure of formula I or a pharmaceutically acceptable salt, solvate or hydrate thereof, wherein, R₁ is straight or branched chain alkyl having 1-4 carbon atoms; and R₂ is phenyl-substituted straight or branched chain alkyl having 1-4 carbon atoms.

In another embodiment, the present invention provides a thiazine amide derivative having a structure of formula I or a pharmaceutically acceptable salt, solvate or hydrate thereof, wherein, R₁ is isobutyl; and R₂ is straight or branched chain alkyl having 1-4 carbon atoms or phenyl-substituted straight or branched chain alkyl having 1-4 carbon atoms.

In another embodiment, the present invention provides a thiazine amide derivative having a structure of formula I or a pharmaceutically acceptable salt, solvate or hydrate thereof, wherein the compound is selected from the following compounds:

(2R)-4-Methyl-2-{[(3R)-4-(toluene-4-sulfonyl)-thiomorpholine-3-carbonyl]-amino}-pentanoic acid, (2R)-4-Methyl-2-{[(3R)-4-(toluene-4-sulfonyl)-thiomorpholine-3-carbonyl]-amino}-pentanoic acid ethyl ester, (2R)-4-Methyl-2-{[(3R)-4-(toluene-4-sulfonyl)-thiomorpholine-3-carbonyl]-amino}-pentanoic acid propyl ester, (2R)-4-Methyl-2-{[(3R)-4-(toluene-4-sulfonyl)-thiomorpholine-3-carbonyl]-amino}-pentanoic acid isopropyl ester, (2R)-4-Methyl-2-{[(3R)-4-(toluene-4-sulfonyl)-thiomorpholine-3-carbonyl]-amino}-pentanoic acid benzyl ester, or the pharmaceutically acceptable salt, solvate or hydrate thereof.

The second aspect of the present invention provides a pharmaceutical composition, comprising the compound mentioned in any embodiment of said first aspect and one or more pharmaceutically acceptable excipients.

In an embodiment, the present invention provides a pharmaceutical composition, wherein, in addition to the compound of any embodiment of said first aspect, the composition also comprises other appropriate pharmaceutical active compounds, and one or more pharmaceutically acceptable excipients.

The third aspect of the present invention provides a use of the compound of any embodiment of said first aspect in preparation of a medicament, wherein the medicament is used for prevention or treatment of neurodegenerative disease caused by physiological or physical injury or progressive lesions.

In an embodiment, the neurodegenerative disease is selected from Alzheimer's disease, Parkinson's disease, Huntington's disease, amyotrophic lateral sclerosis, acquired immunodeficiency-related neuropathy, cerebrospinal multiple sclerosis, stroke or physical stimulation-related brain injury and various neurodegenerative disease affecting central or peripheral nervous system.

The fourth aspect of the present invention provides the compound of any embodiment of the first aspect, wherein the compound is used for prevention or treatment of neurodegenerative disease caused by physiological or physical injury or progressive lesions.

In an embodiment, the neurodegenerative disease is selected from Alzheimer's disease, Parkinson's disease, Huntington's disease, amyotrophic lateral sclerosis, acquired immunodeficiency-related neuropathy, cerebrospinal multiple sclerosis, stroke or physical stimulation-related brain injury and various neurodegenerative disease affecting central or peripheral nervous system.

The fifth aspect of the present invention provides a method for prevention or treatment of neurodegenerative disease caused by physiological or physical injury or progressive lesions in a subject, comprising administering to the subject an effective amount of the compound of any embodiment of the first aspect or the pharmaceutical composition of the second aspect.

In an embodiment, the neurodegenerative disease is selected from Alzheimer's disease. Parkinson's disease, Huntington's disease, amyotrophic lateral sclerosis, acquired immunodeficiency-related neuropathy, cerebrospinal multiple sclerosis, stroke or physical stimulation-related brain injury and various neurodegenerative lesions affecting central or peripheral nervous system.

The compound of the present invention can be prepared via the method as shown in the following reaction route:

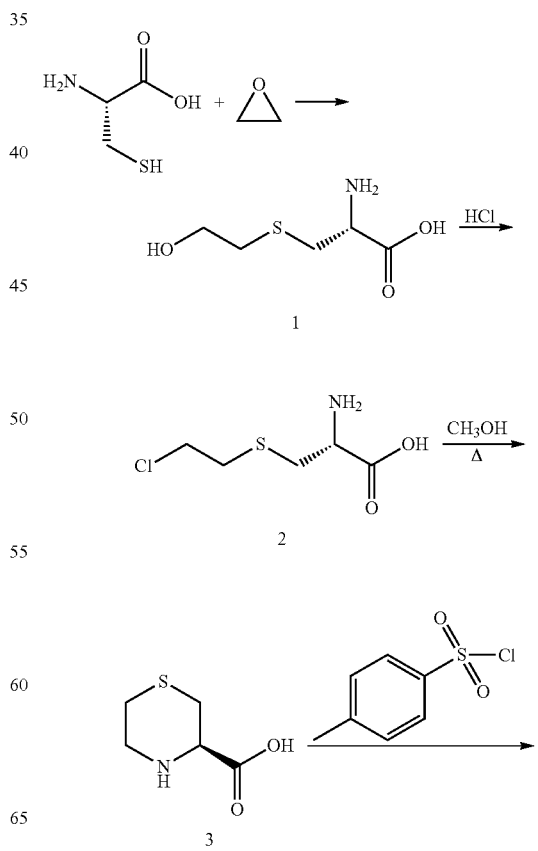

-continued

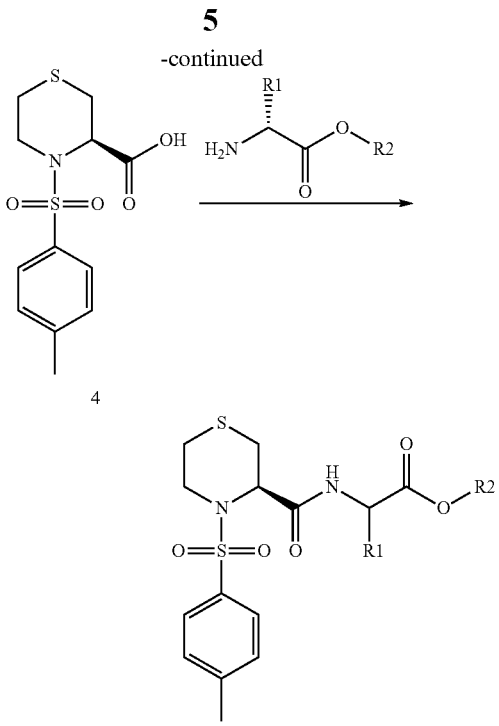

4

When describing the compound of the present invention, the pharmaceutical composition containing the compound, and the method for preventing or treating the neurodegenerative disease caused by physiological or physical injury or progressive lesions of the subject by using the compound, the following terms as used herein have the following meanings. If the terms as used are not specifically defined, the terms have the meanings as generally understood by those skilled in the art.

The term "straight or branched chain alkyl having 1-6 carbon atoms" refers to the straight or branched chain alkyl having 1, 2, 3, 4, 5 or 6 carbon atoms, exemplary groups include methyl, ethyl, n-propyl, isopropyl, n-butyl, isobutyl, tert-butyl, pentyl, hexyl, etc.

Similarly, the term "straight or branched chain alkyl having 1-4 carbon atoms" refers to the straight or branched chain alkyl having 1, 2, 3 or 4 carbon atoms, exemplary groups include methyl, ethyl, n-propyl, isopropyl, n-butyl, isobutyl, tert-butyl, etc.

The term "pharmaceutically acceptable salt" refers to the salt of the compound of the present invention which is pharmaceutically acceptable and has the pharmacological activity of the parent compound. The salt disclosed herein includes those derived from inorganic and organic acids. Examples of inorganic acids include hydrochloric acid, hydrobromic acid, sulfuric acid, nitric acid, phosphoric acid, etc.; examples of organic acids include acetic acid, propionic acid, hexanoic acid, cyclopentyl propionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methanesulfonic acid, ethanesulfonic acid, benzenesulfonic acid, naphthalene sulfonic acid, camphorsulfonic acid, glucoheptonic acid, gluconic acid, glutamic acid, hydroxynaphthoic acid, salicylic acid, stearic acid, muconic acid, etc.; The salt also includes those formed by substitution of acidic protons on the parent compound by metal ions, such as alkali metal ions or alkaline earth metal ions; and coordination compound formed by the parent compound with organic bases, examples of the organic bases include ethanolamine, diethanolamine, triethanolamine. N-methylglucamine, etc.

The term "solvate", unless otherwise specified, refers to a substance formed by complex of the compound of the present invention by a pharmaceutically acceptable solvent. The pharmaceutically acceptable solvent comprises water, ethanol, acetic acid, etc. The solvate comprises those stoichiometric and non-stoichiometric solvate, preferably hydrate.

The compound of the present invention can be crystallized or re-crystallized in water or various organic solvent. In this case, various solvate may be formed.

The term "subject" comprise mammals or human, preferably human.

The term "an effective amount" refers to a dose of the compound which is sufficient to prevent or treat the disease when administered to the subject in need. The "effective amount" can be adjusted according to the compound, the disease and the severity thereof, as well as age, body weight of the treated subject, etc.

The term "treatment" refers to improve or eliminate one or more symptoms of a disease of a subject.

The term "prevention" refers to reduce the risk of a subject suffering from a disease, namely at least one of the clinical symptoms of a disease can be prevented for a subject which may contact or be susceptible to the disease and do not suffer from or show the symptoms of the disease.

The term "pharmaceutically acceptable excipients" refers to any excipients which are conventionally used in the field of pharmaceutical preparations. The selection of specific excipients will depend on administration methods for treating particular patient or disease types and states. For example, the pharmaceutically acceptable excipients comprise conventional diluents, carriers, fillers, binders, humectants, disintegrating agent, absorption enhancers, surfactants, adsorption carriers, lubricants and the like in the pharmaceutical field. If necessary, flavoring agents, preservatives, sweeteners and the like can be added into the pharmaceutical composition. The preparation method of an appropriate pharmaceutical composition for a specific administration mode is well within the scope of knowledge of those skilled in the pharmaceutical field.

The pharmaceutical composition of the present invention can be administered in any ways and any forms commonly used in the art. For example, the pharmaceutical composition of the present invention can be administered in the way selected from the followings: oral administration, spray inhalation, rectal administration, nasal administration, vaginal administration, topical administration, parenteral administration, such as subcutaneous, intravenous, intramuscular, intraperitoneal, intrathecal, intraventricular, intrasternal or intracranial injection, preferably oral administration, intramuscular injection, and intraperitoneal or intravenous injection.

The pharmaceutical composition of the present invention can be made into the form of a unit dose for administration. The dosage forms can be liquid dosage forms or solid dosage forms. The liquid dosage forms can be solution type, colloid type, emulsion type or suspension type and the like. The solid dosage forms can be tablets, powder, suppositories, granules or capsules and the like. Other dosage forms comprise aerosols, implants, patches or liniments and the like.

Generally speaking, it has been proved as advantageous that the dosage of the compound of the present invention is about 1-1000 mg per 24 h, preferably 5-500 mg no matter for human or veterinary use. If appropriate, the daily dosage can be administered in several times by using multiple dose units to achieve the desired effects. The content of the compound of the present invention in the dose unit can be 1-200 mg, preferably 1-100 mg. However, the specific administration dosage depends on the type and the body weight of the subject to be treated, the nature and the severity of the disease, the type of the preparation, the administration mode of the pharmaceutical, the administration period or the time intervals and the like.

According to the present invention, the compound of formula I is able to permeate through blood-brain barrier, and is better than the compound 4 in Chinese patent application No. 01142744.2, thus resulting in a higher bioavailability. Furthermore, as compared with the compound 4 in Chinese patent application No. 01142744.2, the compound of formula I is white crystal, thereby can be readily processed. The compound is stable crystalline with high melting point, the solid of which is loose and has good flowability. Thus, the compound of formula I is suitable for large-scale industrial preparation and processing, in particular to pharmaceutical processing which requires heat or produces heat, such as grinding, drying by heating, fluidized bed drying, high-temperature and high-pressure sterilization and the like. Moreover, the compound of the present invention has a significantly better effect as compared with the compound 4 in Chinese invention patent application No. 01142744.2 in evaluation of anti mouse incomplete cerebral ischemia efficacy.

Based on the experiments completed by the inventors and the results thereof, it is expected that the compound of the present invention can promote nerve growth and regeneration under various neuropathy states, including neurological disease which is related to neuro degeneration, and neuropathies caused by various physical injuries (such as mechanical injury or shock) or diseases (such as diabetes or acquired autoimmune deficiency disease), thus can be used for prevention or treatment of the neurodegenerative disease, such as Alzheimer's disease, Parkinson's disease, amyotrophic lateral sclerosis or stroke.

DETAILED DESCRIPTION OF THE EMBODIMENTS

The following embodiments are exemplary embodiments used for further illustration and should not be construed as limitation to the present invention.

The melting point of a compound was measured by RY-1 melting point apparatus, and thermometer was not calibrated. $^1$H NMR was measured by ARX-400 NMR instrument. Mass spectra was measured by VG-ZabSpec MS instrument. Unless otherwise indicated, all solvent used for reactions was subjected to a standard pretreatment.

Example 1

2-hydroxyethyl cysteine 109 g (0.9 mol) of L-cysteine was added into a 2000 ml round-bottomed flask, dissolved with 1000 ml of distilled water, cooled to 10° C. in ice bath, and neutralized to PH~7 with 24 ml of 1M NaOH solution. 100 ml of ethylene oxide which was pre-cooled was taken at 10° C. and added to the above mixture, the mixture was reacted for 1 h while keeping the temperature at 10° C., then the temperature was raised to room temperature and the reaction was continued for another 1.5 h.

The mixture was extracted with 400 ml×4 of ethyl ether to remove the unreacted ethylene oxide. The aqueous layer was removed by distillation below 60° C., a yellow solid was obtained, re-crystallized with water and ethanol in a ratio of 85 ml:350 ml, filtered, fully washed with 95% ethanol to afford the target compound as white flaky solid, wherein the mp (melting point) was 195-196° C., the weight was about 100 g, and the yield is 67.5%. $^1$H-NMR (400 MHz, D$_2$O) δ: 3.96131 (dd, 1H, J$_1$=4.272 Hz, J$_2$=7.816 Hz), 3.80680-3.77293 (m, 2H), 3.17887 (dd, 1H, J$_1$=4.268 Hz, J$_2$=14.814 Hz), 3.08224 (dd, 1H, J$_1$=7.480 Hz, J$_2$=14.814 Hz), 2.80103 (t, 2H, J=6.036 Hz).

Example 2

2-chloroethyl cysteine hydrochloride 44 g of 2-hydroxyethyl cysteine was added into a 1000 ml round-bottom flask, dissolved in 600 ml of concentrated hydrochloric acid, heated till the external temperature was 90-95° C., stirred and reacted for 7 h. After the reaction, the system was refrigerated and left to stand overnight, and a large number of needle-like solid was precipitated from the system. The solvent was removed by sucking filtration, the obtained solid was naturally dried to give a gray white solid wherein the mp is 185-186° C., the weight is about 40 g, and the yield is more than 70%. $^1$H-NMR (400 MHz, D$_2$O) δ: 4.30477-4.26952 (m, 1H), 3.81913-3.78409 (m, 2H), 3.25903 (dd, 1H, J$_1$=4.444 Hz, J$_2$=14.984 Hz), 3.18877 (dd, 1H, J$_1$=7.352 Hz, J$_2$=15.072 Hz), 3.04410-3.00625 (m, 2H).

Example 3

(3R)-Thiomorpholine-3-carboxylic acid hydrochloride 20 g of 2-chloroethyl cysteine hydrochloride was dissolved in water, added dropwise of NaHCO$_3$ water solution containing 7.2 g of NaHCO$_3$ in an ice bath, after the addition, the mixture was fully stirred for neutralization, extracted with ethyl acetate for three times, the organic phases were combined and dried with Na$_2$SO$_4$.

The solvent was removed under reduced pressure, 400 ml of absolute methanol was added, and the system was stirred at room temperature for 5 days. The solvent was removed under reduced pressure, and the residue was re-crystallized with methanol and ethyl ether to give about 6 g of nearly white solid, wherein the mp is >230° C. $^1$H-NMR (400M Hz, DMSO-d$_6$) δ: 3.67672-3.64308 (m, 1H), 3.55044-3.50108 (m, 1H), 3.16622-3.08322 (m, 1H), 2.92045-2.90326 (m, 1H), 2.83678-2.75406 (m, 2H), 2.61390-2.59272 (m, 1H); MS (FAB) m/z: 148.02.

Example 4

(3R)-4-(Toluene-4-sulfonyl)-thiomorpholine-3-carboxylic acid 13.0 g of (3R)-Thiomorpholine-3-carboxylic acid hydrochloride was suspended in 120 ml of dichloromethane, cooled to 0° C., 30 ml of triethylamine was slowly dropped in, the mixture was stirred for 1 h, then 120 ml of dichloromethane solution dissolved with 13.5 g of p-toluenesulfonyl chloride was slowly dropped in, the resulting mixture was reacted at room temperature for 24 h, filtered to remove a white precipitate, the filtrate was successively washed with saturated sodium bicarbonate solution and water, dried with anhydrous sodium sulfate, the drying agent was removed, dichloromethane was removed by distillation to obtain a white solid, re-crystallized with ethyl acetate and cyclohexane to obtain 19.4 g of white crystals, wherein the yield was 93.5%, the mp was 66° C. (decomp.), and the specific rotation $[\alpha]_D^{24.5}=$ −81.6°($H_2O$). $^1$H-NMR (400 MHz, $CDCl_3$) δ: 7.68268-7.66234 (d, 2H), 7.30642-7.26434 (m, 2H), 5.12406-5.10728 (m, 1H), 4.03322-3.99196 (m, 1H), 3.46642-3.40848 (m, 1H), 3.02301-2.99292 (m, 2H), 2.76875-2.73724 (m, 1H), 2.42688 (s. 3H), 2.38062 (s, 1H).

Example 5

(2S)-4-Methyl-2-{[(3R)-4-(toluene-4-sulfonyl)-thiomorpholine-3-carbonyl]-amino}-pentanoic acid ethyl ester 6 ml (0.042 mol) of TEA was added to a mixture of 4.2 g (0.14 mol) of (3R)-4-(Toluene-4-sulfonyl)-thiomorpholine-3-carboxylic acid, 3.0 g (0.017 mol) of L-leucine ethyl ester hydrochloride, 3.2 g (0.014 mol) of DCC, and 1.7 g (0.014 mol) of DMAP in 200 ml of $CH_2Cl_2$, and the mixture was reacted at room temperature for 24 h. After the reaction, the solid was removed by sucking filtration, the solvent was removed by evaporation, the residue was dissolved with an appropriate amount of ethyl acetate, filtered to remove the insoluble matter, diluted with ethyl acetate, successively washed with 10% of $NaHCO_3$ solution and saturated NaCl solution, dried with $Na_2SO_4$. The drying agent was removed, ethyl acetate was removed by evaporation, the residue was separated by flash chromatographic column (eluent: $CH_2Cl_2$: $CH_3Cl$=1:1), to obtain 4.0 g of oily matter. $^1$H-NMR (400 MHz, $CDCl_3$): δ 7.77237-7.74077 (m, 2H), 7.36382 (d, 2H, J=7.988 Hz), 6.74090 (d, 1H, J=9.244 Hz), 4.80098-4.77466 (m, 1H), 4.68244-4.58898 (m, 1H), 4.28174-4.15708 (m, 3H), 3.53789-3.28674 (m, 1H), 3.13092 (d, 1H, J=13.676), 2.56954-2.42247 (m, 5H), 2.24620-2.20545 (m, 1H), 1.66352-1.53450 (m, 3H), 1.30702-1.26745 (m, 3H), 0.96159-0.91891 (m, 6H); MS (EI) m/z: 443.1, 397.1, 369.1, 287.1, 256.0, 213.1, 155.0, 139.0, 112.0, 91.0, 65.0.

Example 6

(2R)-4-Methyl-2-{[(3R)-4-(toluene-4-sulfonyl)-thiomorpholine-3-carbonyl]-amino}-pentanoic acid ethyl ester According to example 5, (2R)-4-Methyl-2-{[(3R)-4-(toluene-4-sulfonyl)-thiomorpholine-3-carbonyl]-amino}-pentanoic acid ethyl ester was obtained as a white crystal from D-leucine ethyl ester hydrochloride, wherein the yield was 83.5%, the mp was 93-95° C., and the specific rotation $[\alpha]_D^{24.5}=$ −35.4°. $^1$H-NMR (400 MHz, $CDCl_3$): δ 7.77337-7.75377 (d, 2H, J=8.4 HZ), 7.37582-7.264111 (d, 2H, J=8.4 Hz), 6.79090 (d, 1H, J=8.644 Hz), 4.79698-4.58466 (m, 2H), 4.31444-4.08398 (m, 3H), 3.31989-3.11674 (m, 2H), 2.53154-2.45847 (m, 5H), 2.24620-2.21545 (m, 1H), 1.69352-1.65150 (m, 3H), 1.32405-1.27266 (m, 3H), 0.97759-0.94891 (m, 6H); MS (EI) m/z: 443.4, 397.2, 369.2, 263.1, 256.1, 155.0, 139.2, 101.1.

Example 7

(2R)-4-Methyl-2-{[(3R)-4-(toluene-4-sulfonyl)-thiomorpholine-3-carbonyl]-amino}-pentanoic acid propyl ester According to example 5, (2R)-4-Methyl-2-{[(3R)-4-(toluene-4-sulfonyl)-thiomorpholine-3-carbonyl]-amino}-pentanoic acid propyl ester was obtained as a white crystal from D-leucine propyl ester hydrochloride, wherein the yield was 87.5%, the mp was 96-98° C., and the specific rotation $[\alpha]_D^{24.5}=$ −38.1° ($CH_3OH$). $^1$H-NMR (400 MHz, $CDCl_3$): δ 7.76337-7.74277 (d, 2H, J=8.4 HZ), 7.37782-7.35712 (d, 2H, J=8.4 Hz), 6.76390-6.74745 (d, 1H, J=8.644 Hz), 4.79598-4.70066 (m, 2H), 4.28444-4.08098 (m, 3H), 3.54489-3.53274 (t, 1H, J=2.6 HZ), 3.14892 (d, 1H, J=13.676), 2.56954-2.42247 (m, 5H), 2.23720-2.19945 (m, 1H), 1.70552-1.62350 (m, 5H), 0.95459-0.93291 (m, 9H); MS (EI) m/z: 457.3, 397.2, 369.3, 256.2, 174.0, 118.1, 101.1.

Example 8

(2R)-4-Methyl-2-{[(3R)-4-(toluene-4-sulfonyl)-thiomorpholine-3-carbonyl]-amino}-pentanoic acid isopropyl ester According to example 5, (2R)-4-Methyl-2-{[(3R)-4-(toluene-4-sulfonyl)-thiomorpholine-3-carbonyl]-amino}-pentanoic acid isopropyl ester was obtained as a white crystal from D-leucine isopropyl ester hydrochloride, wherein the yield was 91.5%, the mp was 89-91° C., and the specific rotation $[\alpha]_D^{24.5}=$ −43.9° ($CH_3OH$). $^1$H-NMR (400 MHz, $CDCl_3$): δ 7.76237-7.74077 (d, 2H J=8.208 Hz), 7.37382-7.26511 (d, 2H, J=8.208 Hz), 6.75090 (d, 1H, J=8.944 Hz), 5.40112 (m. 1H), 4.79298-4.25166 (m, 3H), 3.54989-3.53674 (t, 1H, J=12.31110), 3.15292-3.11800 (d, 1H, J=13.676 HZ), 2.56054-2.46247 (m, 4H), 2.23220-2.20345 (m, 1H), 1.62552-1.43450 (m, 4H), 1.26202-1.24745 (m, 6H), 0.94659-0.93191 (m, 6H); MS (EI) m/z: 457.3, 397.2, 369.2, 256.2, 154.7, 101.1.

Example 9

(2R)-4-Methyl-2-{[(3R)-4-(toluene-4-sulfonyl)-thiomorpholine-3-carbonyl]-amino}-pentanoic acid benzyl ester According to example 5, (2R)-4-Methyl-2-{[(3R)-4-(toluene-4-sulfonyl)-thiomorpholine-3-carbonyl]-amino}-pentanoic acid benzyl ester was obtained as a white crystal from D-leucine benzyl ester hydrochloride, wherein the yield was 83.5%, the mp was 91-93° C., and the specific rotation $[\alpha]_D^{24.5}=$ −33.1° ($CH_3OH$). $^1$H-NMR (400 MHz, $CDCl_3$): δ 7.75237-7.71377 (d, 2H, J=1.2 HZ), 7.36382-7.26322 (m, 7H), 6.73090 (m, 1H), 5.18600-5.11600 (2H, m), 4.78698-4.75466 (m, 2H), 4.24244-4.10298 (m, 1H), 3.37689-3.09274 (m, 2H), 2.52054-2.44547 (m, 5H), 2.06820-2.04745 (m, 1H), 1.66552-1.25450 (m, 3H), 0.92259-0.90691 (m, 6H); MS (EI) m/z: 505.6, 475.1, 457.6, 434.7, 399.0, 370.8, 336.7, 308.3, 272.4, 232.6, 148.8, 106.5.

Example 10

(2R)-4-Methyl-2-{[(3R)-4-(toluene-4-sulfonyl)-thiomorpholine-3-carbonyl]-amino}-pentanoic acid According to example 5, (2R)-4-Methyl-2-{[(3R)-4-(toluene-4-sulfonyl)-thiomorpholine-3-carbonyl]-amino}-pentanoic acid was obtained as a white crystal from D-leucine, wherein the yield was 77.5%, the mp was 87-89° C., and the specific rotation $[\alpha]_D^{24.5}=$ −86.7° ($H_2O$). $^1$H-NMR (400 MHz, $CDCl_3$): δ 7.75337-7.73377 (d, 2H, J=8.4 HZ), 7.36582-7.254111 (d, 2H, J=8.4 Hz), 6.78090 (d, 1H, J=8.644 Hz), 4.32444-4.09398 (m, 3H), 2.52154-2.44847 (m, 5H), 2.25620-2.22545 (m, 1H), 1.68352-1.44150 (m, 4H), 0.99759-0.96891 (m, 6H); MS (EI) m/z: 414.6.

Example 11

Evaluation of Neurotrophic Activity of the Compound

The neurotrophic activity of the compound of the present invention can be reflected on a variety of in-vitro biological models, such as an in-vitro serum-free culture model of chicken embryonic dorsal root ganglia. Chicken embryo incubated for 8 d was used, and spine and ganglia on the two sides were exposed under a dissecting microscope in sterile environment. The dorsal root ganglia was picked one by one with tweezers, inoculated into culture bottles laid with rat tail collagen according to 5-6 dorsal root ganglia per bottle, two bottles were prepared per dose, and cultured at 37° C., 5% of $CO_2$, for 1 h in an incubator for adherence, then added with a serum-free culture medium DMEM containing NGF (0.15 ng/mL) and the compound of the present invention, while the control group was only added with the culture medium and the same dose of NGF. After being cultured in the incubator for 48 h, the growth of the neurite around dorsal root ganglia was observed under an inverted phase contrast microscope and scored according to the length and density of the neurite, wherein 0 point represents no neurite; 1 point represents the neurite was sparse; 2 points represent the neurite was relatively long or dense; and 3 points represent the neurite was long and dense. The score of the growth of neurite of chicken embryonic dorsal root ganglion under the promotion of the compound of the present invention with different dosage was shown in table 1, wherein each score is an average of five dorsal root ganglia.

TABLE 1

Evaluation Results of Activity of Compounds
in Promotion of Chicken Embryonic Dorsal Root

| Group | Mean score |
| --- | --- |
| Culture medium + NGF (0.15 ng/mL) (control group) | 0.33 |
| Example 5 (1 pM) + NGF (0.15 ng/mL) | 0.65 |
| Example 5 (100 pM) + NGF (0.15 ng/mL) | 1.55 |
| Example 6 (1 pM) + NGF (0.15 ng/mL) | 1.23 |
| Example 6 (100 pM) + NGF (0.15 ng/mL) | 1.88 |
| Example 7 (1 pM) + NGF (0.15 ng/mL) | 1.46 |
| Example 7 (100 pM) + NGF (0.15 ng/mL) | 1.95 |
| Example 8 (1 pM) + NGF (0.15 ng/mL) | 1.68 |
| Example 8 (100 pM) + NGF (0.15 ng/mL) | 2.25 |

Example 12

In-Vivo Pharmacodynamics Evaluation of Compounds for Stroke

1. Experimental Scheme

The example, which took Kunming mice as experimental subjects, investigated the protection of prevention administration of the compound of the present invention against incomplete cerebral ischemia of mice, through intravenous and intragastric administration, on mouse bilateral carotid artery occlusion with low blood pressure (BCAO-LBP) model, by measuring neurological function score and MDA content in brain.

2 Experimental Methods 2.1 Drug Preparation 2.1.1 Preparation of 0.7% CMC-Na: on the day before use, 0.7 g (700 mg) of CMC-Na dry powder was weighted, added into 100 ml of distilled water, the mixture was heated and stirred moderately, and allowed to stand overnight to fully and uniformly mixed after completely dissolved, seal preservation.

2.1.2 Preparation of drug for intragastric administration: the compound of the present invention was made into 30 mg/kg by using 0.7% CMC-Na, fully and uniformly mixed with sonication to afford a solution of 1.5 mg/ml. Intragastric (i.g) administration was performed according to 0.2 ml/10 g.

2.1.3 Preparation of 10% DMSO: 1000 µL of DMSO (analytically pure) was transferred to 9 ml of N.S. with a micropipette and uniformly mixed. Prepare when needed.

2.1.4 Preparation of drug for intravenous administration: the compound of the present invention was firstly dissolved with a small amount of DMSO, N.S. was added to reach the required volume after several minutes and fully and uniformly mixed to give the solution of 1 mg/ml (the final concentration of the DMSO was 10%), prepare when needed. The solution was injected to caudal vein according to 0.1 ml/10 g, wherein the dosage in mice was 10 mg/kg.

2.2 Group and Administration 2.2.1 Observation of anti-cerebral ischemia effect of compounds of the present invention by intragastric administration 28 mice which had adapted to the laboratory environment for one week were divided into balanced groups according to body weight, i.g administered respectively with 0.7% CMC-Na or the compound of the present invention, once per day for continuous 3 d. The specific groups were as follows:

sham operation group: 4 mice, with i. g of 0.7% CMC-Na solution cerebral ischemia model group: 12 mice, with i. g of 0.7% CMC-Na solution drug group: 12 mice, with i. g of solution of compounds of the present invention separately, wherein the dosage was 30 mg/kg 2.2.2 Observation of Anti-Cerebral Ischemia Effect of Compounds of the Present Invention by Intravenous Administration 28 mice which had adapted to the laboratory environment for one week were divided into balanced groups according to body weight, i. v administered with 10% DMSO or the compound of the present invention, respectively, once per day for continuous 3 d. The specific groups were as follows:

sham operation group: 4 mice, with i. v of 10% DMSO solution model group: 12 mice, with i. v of 10% DMSO solution drug group: 12 mice, with i. v of solution of compounds of the present invention separately, wherein the dosage was 10 mg/kg 2.3 Determination of Incomplete Global Cerebral Ischemia and MDA Content in Brain of the Mice 2.3.1 Mouse bilateral carotid artery ligation: the mouse was performed with orbit bloodletting (about 30% of the total blood volume of the mouse) to lower the blood pressure 1 h later after last administration, then the mouse was fixed on an operation plate in a supine position, and an incision in the middle of the neck was made. The common carotid artery was exposed with blunt separation, and 2 sutures were prepared under each end of the exposed artery, and both end of the artery were ligatured, respectively. When the ligation was completed for the third suture, started timing, then cut the common carotid artery between the two ligations, and the incision was sutured. In the sham operation group, the common carotid artery was separated without ligation. The mouse was rapidly released after the operation, the behavior in 6 h and the death time of the mouse was observed and recorded (scored by a blind method according to the following table). The brain was quickly took out after death, the cerebellum was removed, and the MDA content in the whole brain was determined by a TBA method. The mouse which did not die until 6 h, was put to death and taken the brain.

2.3.2 Neural function score: the scoring standard was shown in Table 2.

TABLE 2

Neurobehavioral Evaluation Table

| | |
|---|---|
| (1) Place the mouse on the ground (If several following behaviors simultaneously occur, record as the most serious behavior; if the mouse does not move, gently push the buttock to stimulate the mouse to move) | 4 points |
| Normal activities | 0 point |
| Bent walking route, but no circling (no appearance of rear-end phenomenon) | 1 point |
| Circling, with appearance of rear-end phenomenon (record the rotation direction, clockwise or counter-clockwise) | |
| circling for 1-2 times | 1 point |
| Circling for 3-5 times | 2 points |
| Circling for more than 5 times | 3 points |
| Rolling (record the rolling direction, left or right) | |
| rolling for 1-2 times | 1 point |
| Rolling for 3-5 times | 2 points |
| Rolling for more than 5 times | 3 points |
| Hemiplegia (record the hemiplegia direction, left or right) | 4 points |
| (2) Abnormal Activities | 8 points |
| Dystonia (torsional involuntary movements, resulting in postures which are persistent and often weird), seizures (sudden loss of consciousness, falling to the ground, hypsokinesis of head and rigidity of limbs) and myoclonus (convulsions) | 1 point |
| Exciting (jumping) | |
| jumping for 1-2 times | 1 point |
| Jumping for 3-5 times | 2 points |
| Jumping for more than 5 times | 3 points |
| Stationary or wheezing occasionally(if hemiplegia occurs, record the hemiplegia) | 2 points |
| 4 points: dead immediately after an operation (within 10 min) | |
| (3) Loss of reflexes | 1 point |
| Pinna reflexes (the mouse shakes the head when the ear canal of the mouse is touched) | 1 point |
| | Total 13 points |

2.3.3 Determination of MDA Content in Brain of Mice

The brain of a mouse was taken out, weighted, prepared into 15% brain homogenate with N.S, 1.2 ml of the homogenate was taken out and put into a 37° C. water bath for 1 h (shaked once every 10 min), then taken out from water, added with 0.6 ml of 20% trichloroacetic acid, uniformly mixed, and stood for 10 min, centrifugated at 2000 r for 10 min, 1.2 ml of supernatant fluid was added with 0.6 ml of 0.67% TBA, and put into a boiling water bath for 10 min, then cooled, and OD value was determined at 532 nm.

3. Statistical Analysis

Experimental data was represented by $\bar{x}\pm SEM$, SPSS13.0 statistical software was applied, homogeneity of variance was judged by single-factor variance analysis. The homogeneity of variance was tested by LSD, the non-homogeneity of variance was tested by Dunnett's T3, the significant differences between the groups were compared and $P<0.05$ represented a statistical significance. The results were shown in Table 3.

TABLE 3

MDA Content and Neurobehavioral Score Evaluation Results of Compounds on BCAO-LBP Mice ($\bar{x} \pm$ SEM)

| Treatment (i.g) | n | MDA content (nmol/g) | Neural deficit score |
|---|---|---|---|
| Control | 4 | 33.15 ± 2.75 | 0.00 ± 0.00 |
| Medium | 11 | 40.94 ± 1.754* | 3.92 ± 0.25** |
| Example 5 (30 mg/kg) | 12 | 36.09 ± 1.85 | 3.62 ± 0.31 |
| Example 6 (30 mg/kg) | 12 | 30.87 ± 0.95### | 3.08 ± 0.40 |
| Example 7 (30 mg/kg) | 11 | 34.90 ± 1.65## | 2.91 ± 0.28 |
| Example 8 (30 mg/kg) | 12 | 33.27 ± 1.91## | 2.67 ± 0.31# |

*$p < 0.05$, compared with the control group;
**$p < 0.01$, compared with the control group;
$p < 0.05$, compared with the medium group;
$p < 0.01$, compared with the medium group;
$p < 0.001$, compared with the medium group; analyzed with ANOVA followed LSD on SPSS 13.0 is used for analysis.

Example 13

Evaluation of Blood-Brain Barrier Permeability and Researches on Membrane Permeability of MDCK-MDR1 Cells of the Compounds 1. Experimental Scheme MDCK-MDR1 cells are monolayer cells with high expression of a P-gp transporter after MDR1 genes are transfected in MDCK (Madin-Darby canine kidney epithelial cells). Due to the compactness of the monolayer cells and high expression of a pharmaceutical efflux protein, the cells have a similarity to the structure of the blood-brain barrier (BBB), and can be used as one of the models for evaluating the BBB permeability. Because the compounds of the present invention targeted at the central nervous system and were needed to permeate the BBB, the MDCK-MDR1 cells were applied to research the membrane permeability, and the BBB permeability was preliminarily evaluated.

2 Experimental Methods 2.1 Solution Preparation

Preparation of a culture solution: when in use, DMEM was added with 10% FBS, 1% glutamine, 100 U·mL$^{-1}$ of penicillin and streptomycin double-antibiotic solution, 1% non-essential amino acids, and 1.2 mg·L$^{-1}$ of G418.

Preparation of a digestion solution: 1 g of trypsin and 80 mg of EDTA were weighted, added with 400 mL of phosphate buffer solution, filtered with a 0.22 μm filter membrane to remove bacteria, and stored at −20° C. for later use.

Preparation of a glutamine stock solution: 2.92 g of glutamine was added with 100 mL of PBS buffer solution, filtered with 0.22 μm filter membrane to remove bacteria, sub-packaged in 1 mL, and stored at −20° C. for later use.

Preparation of a penicillin and streptomycin stock solution: 0.8 million U of penicillin was added with 20 mL of saline; 1 million U of streptomycin was added with 25 mL of saline; the two solution were uniformly mixed in a ratio of 1:1, filtered with 0.22 μm filter membrane to remove bacteria, sub-packaged in 1 mL, and stored at −20° C. for later use.

Preparation of an HBSS solution: 8.0 g of NaCl, 0.4 g of KCl, 0.0475 g of Na$_2$HPO$_4$—H$_2$O, 0.06 g of KH$_2$PO$_4$ and 6 g of Hapes were added into ultra-pure water for dissolution, the pH value was adjusted to 7.2-7.4, water was added till 1 L, filtered with 0.22 μm filter membrane to remove bacteria, and stored at −20° C. for later use.

2.2 Cell Culture

The cryopreserved MDCK-MDR1 cells were fast thawed in a 37° C. water bath. The postthawed cells were added into a DMEM culture medium containing 10% FBS, cultured in an incubator at 37° C., 5% $CO_2$, with the relative humidity of 90%, and the culture medium was replaced every other day. After 1-2 days' growth for cell fusion, the cells were digested at 37° C., with the mixed digestion solution of 0.25% trysin-EDTA (0.2%), and subcultured according to a certain ratio, wherein the cells used for the experiment are 40~60-generation cells.

When 80% of the cells were fused, the cells were suspended with a complete culture medium, and inoculated into a Millicell plate according to $1\times10^6 \cdot mL^{-1}$. The culture solution was changed once every two days, then once every day after 1 week. After cultured for 5 days, the cells were ready for transport experiment when the resistance achieves a platform (>2000 Ω·cm²).

2.3 Quality Control of MDCK-MDR1 Monolayer Cells:

2.3.1 Measurement of Transepithelial Electrical Resistance (TEER)

When the transepithelial electrical resistance was measured, the electrode was firstly immersed in DMEM culture solution and balanced for 24 h, then the electrode was took out and immersed into 70% alcohol and sterilized for 15 min, then placed at room temperature, naturally dried, and further placed into the sterile DMEM culture solution and balanced for 15 min. During the experiment, the two ends of the electrode was sequentially inserted into the upper and lower pools of each well of a 24-well Millicell culture plate to detect the resistance, any point in each well was measured for three times, the resistance was recorded, the resistance of a blank well was measured simultaneously, and the transepithelial electrical resistance (TEER) was calculated according to the following formula:

TEER=$(Rt-R0)\times S$ wherein, Rt is the measured resistance; R0 is the resistance of the blank well; and S is effective membrane area.

2.3.2 Quality Control of Positive Compound:

Rho-123 (Rhodamine 123) was taken as a positive quality control compound, diluted to 5 $\mu mol \cdot L^1$ with HBSS, the culture medium in the wells was firstly suction abandoned before the experiment, the wells were washed with HBSS solution at 37° C. for two times, then incubated in incubator at 37° C., Rho-123 was added into the upper pools, HBSS solution was added into the lower pools, and the wells were incubated in a constant-temperature shaker. The solution in the lower pools was collected at 0, 30, 90 and 120 min and stored at −20° C. for later measurement. The permeation amount of the Rho-123 in the lower pools was detected by a fluorescence spectrophotometer, wherein the transmission wavelength was set to 430 nm and the excitation wavelength was set to 530 nm. The Papp value of Rho-123 in the experiment is accorded with literature reports.

2.4 Pharmaceutical Transport Experiment

The Millicell inoculated with cells was soaked with HBSS solution at 37° C. for an appropriate time before the test, and slightly flushed to remove matters attached on the surfaces of the cells. Permeability from the cavity surface to the basal surface: 0.35 mL of drug contained HBSS solution was added from the apical side (AP), while 1.2 mL of blank HBSS solution was added from the basolateral side (BL), placed at 37° C., shaked at 50 $r \cdot min^{-1}$, 50 μL was sampled from the lower layer at 0, 30, 90 and 120 min separately, and the same volume of blank HBSS solution was supplemented. Each concentration was repeated in three wells, the sample was precisely added with 50 μL of internal standard solution and 350 μL of ethyl acetate, shaked and uniformly mixed, centrifugated at 12000 rmp for 5 min, 300 μL of supernatant was took, volatilized to dryness, re-dissolved with 50 μL of acetonitrile and 10 μL was took for sampling and determination. Permeability from the basal surface to the cavity surface: drug was added from the basolateral side (BL), while the blank HBSS solution was added from the apical side (AP), and the following steps were same as those in the permeability test from the cavity surface to the basal surface.

The apparent permeability coefficient (Papp) of the drug reflected the capability of permeating the monolayer cells of the drug and the absorption speed and degree of the drug, which can be calculated by the following formula:

$$P_{app} = \frac{\Delta Q}{\Delta t \cdot A \cdot C_0}$$

wherein, ΔQ was the permeation amount of the drug in a Δt time period, A was the surface area of the cells, namely the area (0.6 cm²) of a support membrane in the model, and C0 was the initial concentration. The unit of the Papp was commonly represented by $cm \cdot h^{-1}$ or $cm \cdot s^{-1}$.

2.5 Sample Detection

The sample was detected by LC/MS. Concentration of each sample was quantified with a standard curve (50 nM-10000 nM).

3. Experimental results

| Drugs | $P_{app}(\times 10^{-6})$ |
| --- | --- |
| Rhodamine 123 | 4.89 |
| Example 6 | 19.2 |
| Example 7 | 49.8 |
| Example 8 | 39.5 |
| Example 9 | 12.4 |
| Example 10 | 34.1 |
| Example 5 | 8.38 |

What is claimed is:

1. A thiazine amide derivative having a structure of formula I,

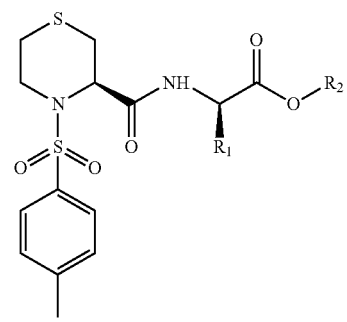

wherein,
$R_1$ is isobutyl; and
$R_2$ is a straight or branched chain alkyl having 1-4 carbon atoms,
or a pharmaceutically acceptable salt, solvate or hydrate thereof.

2. A compound selected from the group consisting of:
(2R)-4-Methyl-2-{[(3R)-4-(toluene-4-sulfonyl)-thiomorpholine-3-carbonyl]-amino}-pentanoic acid,
(2R)-4-Methyl-2-{[(3R)-4-(toluene-4-sulfonyl)-thiomorpholine-3-carbonyl]-amino}-pentanoic acid ethyl ester, (2R)-4-Methyl-2-{[(3R)-4-(toluene-4-sulfonyl)-thiomorpholine-3-carbonyl]-amino}-pentanoic acid propyl ester, and (2R)-4-Methyl-2-{[(3R)-4-(toluene-4-sulfonyl)-thiomorpholine-3-carbonyl]-amino}-pentanoic acid isopropyl ester, or a pharmaceutically acceptable salt, solvate or hydrate thereof.

3. A pharmaceutical composition, comprising the compound according to claim 1 or 2, or a pharmaceutically acceptable salt, solvate or hydrate thereof, and one or more pharmaceutically acceptable excipients.

4. A method for treatment of neurodegenerative disease caused by physiological or physical injury or progressive lesions in a subject, wherein the neurodegenerative disease is selected from the group consisting of Alzheimer's disease, Parkinson's disease, Huntington's disease, amyotrophic lateral sclerosis, acquired immunodeficiency-related neuropathy, cerebrospinal multiple sclerosis and stroke, comprising administering to the subject an effective amount of the compound according to claim 1 or 2 or a pharmaceutically acceptable salt, solvate or hydrate thereof.

5. A method for treatment of neurodegenerative disease caused by physiological or physical injury or progressive lesions in a subject, wherein the neurodegenerative disease is selected from the group consisting of Alzheimer's disease, Parkinson's disease, Huntington's disease, amyotrophic lateral sclerosis, acquired immunodeficiency-related neuropathy, cerebrospinal multiple sclerosis and stroke, comprising administering to the subject an effective amount of the pharmaceutical composition according to claim 3.

* * * * *